(12) United States Patent
Becker et al.

(10) Patent No.: US 7,108,985 B2
(45) Date of Patent: Sep. 19, 2006

(54) METHODS AND KITS USEFUL FOR THE SIMPLIFICATION OF COMPLEX PEPTIDE MIXTURES

(75) Inventors: Christopher Becker, Palo Alto, CA (US); James R. LaDine, Whitinsville, MA (US); Thomas A. Shaler, Fremont, CA (US); Chia-Hui Paul Shieh, Fremont, CA (US)

(73) Assignee: Thermo Finnigan, LLC, San Jose, CA (US)

( * ) Notice: Subject to any disclaimer, the term of this patent is extended or adjusted under 35 U.S.C. 154(b) by 447 days.

(21) Appl. No.: 10/115,301

(22) Filed: Apr. 3, 2002

(65) Prior Publication Data

US 2002/0168691 A1   Nov. 14, 2002

Related U.S. Application Data

(60) Provisional application No. 60/281,244, filed on Apr. 3, 2001.

(51) Int. Cl.
   G01N 33/53     (2006.01)
   G01N 24/00     (2006.01)
   G01N 33/532    (2006.01)
   G01N 33/534    (2006.01)
   C12Q 1/37      (2006.01)
   C07K 1/10      (2006.01)
   C07K 1/14      (2006.01)

(52) U.S. Cl. .......................... 435/7.1; 435/7.5; 435/23; 436/173; 436/544; 436/545; 436/824; 530/402; 530/409; 530/412

(58) Field of Classification Search ............... 435/7.5, 435/7.1, 23; 436/518, 173, 544, 545, 824; 530/402, 409, 412
See application file for complete search history.

(56) References Cited

U.S. PATENT DOCUMENTS 5,840,867 A * 11/1998 Toole et al. ............... 536/23.1
6,218,111 B1   4/2001 Southern et al. ............... 435/6
6,322,970 B1  11/2001 Little et al. ................... 435/6
6,383,742 B1   5/2002 Drmanac et al. ............. 435/6

FOREIGN PATENT DOCUMENTS

WO   WO 00/11208   3/2000
WO   WO 02/37121   5/2002

OTHER PUBLICATIONS

Geoghegan et al., Site-directed conjugation of nonpeptide groups to peptides and proteins via periodate oxidation of a 2-amino alcohol. Application to modification at N-terminal serine. Bioconjugate Chem. 1992, vol. 3. pp. 138-146.*
Gygi et al. "Quantitative Analysis of Complex Protein Mixtures Using Isotope-Coded Affinity Tags" Nature Biotechnology 17:994-999, 1999.
Rose et al., "New Cyclization Reaction at the Amino Terminus of Peptides and Proteins" Bioconjugate Chem. 10(6):1038-1043, 1999.
Rose et al., "Natural Peptides as Building Blocks for the Synthesis of Large Protein-Like Molecules with Hydrazone and Oxime Linkages" Bioconjugate Chem. 7(5):552-557, 1996.
Rose, K., "Facile Synthesis of Homogenous Artificial Proteins" J. Am. Chem. Soc. 116:30-33, 1994.

* cited by examiner

Primary Examiner—Long V. Le
Assistant Examiner—Shafiqul Haq
(74) Attorney, Agent, or Firm—Fish & Richardson P.C.

(57) ABSTRACT

Methods and reagents for obtaining simplified mixtures of peptides from a sample containing a number of peptides are disclosed. The simplified sample can be easier to analyze than the original peptide sample yet it is representative of all or nearly all of the proteins present in the mixed protein sample from which the original and more complex peptide sample was derived. The methods entail the use of tagging moieties that include an amino-acid-specific reactive group (R). The tagging moieties "tag" peptides or proteins at specific amino acids (e.g., by reacting with an amino acid to form a covalent bond), ultimately allowing the isolation of peptides that contain those specific amino acids. Other methods entail the used of a reactive moiety ($R_P$) that comprises a reagent that selectively interacts with selected proteins, either covalently or noncovalently. For example, $R_P$ can be a natural ligand for a receptor that is to be tagged or a protein that interacts with a second protein that is to be tagged. It can be an enzymatic substrate or other element of molecular recognition such as an antibody, ATP, GTP, NAD, NADP, NADH, NADPH, ubiquitin, or structural analogs thereof.

24 Claims, 6 Drawing Sheets

METHODS AND KITS USEFUL FOR THE SIMPLIFICATION OF COMPLEX PEPTIDE MIXTURES

RELATED APPLICATION INFORMATION

This application claims priority from provisional application serial No. 60/281,244, filed Apr. 3, 2001, hereby incorporated by reference.

BACKGROUND OF THE INVENTION

Proteomic techniques that permit the identification, quantification, and localization of proteins in cells will advance the understanding of cell function and development far beyond what has been achieved by genomic techniques. For example, the ability of advanced mass spectrometry techniques to analyze complex protein mixtures, e.g., multi-protein complexes, cell fractions and whole cells extracts, promises to provide powerful high throughput diagnostic and screening methods.

Mass spectrometry can be used to identify single proteins or large number of proteins in mixtures. In addition, mass spectrometry can be used to sequence a peptide de novo. For example, tandem mass spectrometry of peptides generated by proteolytic digestion of a complex protein mixture (e.g., a cell extract) can be used to identify and quantify the proteins present in original mixture. This result can be achieved because tandem mass spectrometers capable of selecting single m/z values and subjecting the ions to collision induced disassociation (CID) can be used to sequence and identify peptides. The information created by CID of a peptide can be used to search protein and nucleotide sequence databases to identify the amino acid sequence represented by the spectrum and thus identify the protein from which the peptide was derived.

Tandem mass spectrometry used to identify a peptide in a complex mixture of peptides derived from digested proteins utilizes three types of information. First, the mass of the peptide is obtained. This information alone can greatly reduce number of possible peptide sequences, particularly if the protein was digested with a sequence specific protease. The second type of information is the pattern of fragment ions produced by CID of the peptide ion. Analytical methods that compare the fragment ion pattern to theoretical fragment ion patterns generated computationally from sequence databases can be used to identify the peptide sequence. Such methods can identify the best match peptides and statistically determine which peptide sequence is more likely to be correct. The accuracy of the predictions can be increased further by using multiple dimensions of MS analysis to obtain de novo the sequence of a portion of a peptide. This direct sequence information can be used to further increase the accuracy of the prediction based on the fragment ion patterns. Once the peptide is identified, the protein from which it was generated can be readily determined by searching sequence databases.

Proteins in complex mixtures, e.g., cell extracts, can be identified by a combination of enzymatic proteolysis, liquid chromatographic separation, tandem mass spectrometry, computer algorithms which correlate peptide mass spectra to those theoretically predicted based on sequence databases and by de novo sequencing.

Electrospray ionization permits liquid chromatography to be directly coupled to a tandem mass spectrometer so that complex mixtures can be temporally separated prior to introduction into the mass spectrometer. The increase in the number of organisms for which a complete genome sequence is available will greatly increase the value of this approach to the analysis of complex mixtures.

SUMMARY OF THE INVENTION

The invention features methods and reagents for obtaining simplified mixtures of peptides from a sample containing a number of peptides, e.g., a sample created by proteolytic digestion of a mixture of proteins, e.g., a mixture of proteins obtained from a biological sample. The methods and reagents of the invention can be used to decrease the number of peptides (or proteins) in the sample according to a rational and controlled scheme so as to obtain a simplified peptide sample containing fewer peptides. For example, starting with a peptide sample created by proteolytic digestion of a mixed protein sample, one can obtain a simplified peptide sample that contains only one or a few of the peptides created by proteolytic digestion of each the proteins in the mixed protein sample. The simplified sample can be easier to analyze than the original peptide sample yet it is representative of all or nearly all of the proteins present in the mixed protein sample from which the original and more complex peptide sample was derived. Accordingly, the simplified peptide mixture can be used to identify and quantify all or nearly all of the proteins in the original mixed protein sample. The simplified mixture is useful even when it does not include at least one peptide from each of the proteins in the mixed proteins sample since in some cases it is not necessary to identify or quantify all of the proteins in the mixed protein sample.

The methods and compositions of the invention are useful for analyzing peptides that are generated by the enzymatic digestion of complex protein mixtures (e.g., cell extracts). The methods and compositions of the invention are useful in any setting in which it is desirable to reduce the complexity of a peptide mixture in a controlled and specific manner and find particular application in the preparation of peptide samples for analysis by mass spectrometry.

The methods of the invention entail the use of tagging moieties that include an amino-acid-specific reactive group (R). The tagging moieties "tag" peptides or proteins at specific amino acids (e.g., by reacting with an amino acid to form a covalent bond), ultimately allowing the isolation of peptides that contain those specific amino acids. The amino acid tagged by a given tagging moieties depends on the identity of the R group present on the moiety. One R group ($R_{S/T}$) tags serines (ser) and threonines (thr) when they are present at the amino terminus of a peptide. Another R group ($R_C$) tags cysteines (cys), present anywhere in a peptide, at its thiol group. Another R group ($R_L$) tags lysines (lys), present anywhere in a peptide, at its primary amine The invention also features a reactive moiety ($R_P$) that comprises a reagent that selectively interacts with selected proteins, either covalently or noncovalently. For example, $R_P$ can be a natural ligand for a receptor that is to be tagged or a protein that interacts with a second protein that is to be tagged. It can be an enzymatic substrate or other element of molecular recognition such as an antibody, ATP, GTP, NAD, NADP, NADH, NADPH, ubiquitin, or structural analogs thereof. $R_P$ is a special case of R as its use is intended to simplify peptide samples by selectively reducing the number of proteins appearing in the mixed protein sample prior to proteolysis.

The reactive group of the tagging moiety is directly or indirectly associated with other groups that facilitate the isolation of tagged peptides. Thus, the tagging moiety can include a linker group (L) which can connect the R group to a group (B or M) that facilitates the capture of tagged peptides. The B group is a group, e.g., biotin that can selectively bind to a capture reagent, e.g., strepavidin. The M group is a magnetic particle that can be attracted by a magnetic force.

The isolated peptides can be analyzed by mass spectrometry or any other desired method. For example, Mass spectrometry can be used to identify and/or quantify one or more of the peptides in the simplified mixture.

Thus, the invention features a method for reducing the number of peptides present in a sample, the method comprising: (a) providing a tagging moiety comprising three covalently-connected parts:

R-L-B wherein R is a reactive group (for example: $R_{S/T}$, $R_C$, $R_L$ or $R_P$) that reacts with peptides or proteins; L is a linker group containing zero or more atoms in a straight or branched chain and an optional selective cleavage site; and B is a group that can selectively bind to a capture reagent; (b) reacting the sample with the tagging moiety to provide tagged peptides or proteins; (c) contacting the tagged peptides or proteins with a capture reagent to provide captured tagged peptides or proteins and isolating the captured tagged peptides or proteins from other material in the sample (e.g., non-tagged peptides or proteins); (d) releasing at least the peptide portion or protein portion of the tagged peptide or protein from the capture reagent to provide released modified peptides or proteins; and (e) analyzing the released modified peptides or proteins, or fragments thereof, by mass spectrometry to identify at least one peptide or protein present in the sample. The released modified peptide or protein can include all or part of R and all or part or none of L.

In addition, the invention optionally features the moiety R-L*-B where L* is isotopically labeled version of L. Such isotopically labeled tagging moieties provide a means for quantifying two or more samples each labeled differently from each other and subsequently mixed together prior to mass analysis. The isotopic label can be $^2H$, $^{13}C$, $^{15}N$, $^{18}O$, $^{34}S$, or any other suitable isotopic label. The invention also optionally features R*-L-B and R-L-B* were B* is an isotopically labeled version of B and R* is an isotopically labeled version of R. The moiety can also provide a means for obtaining differentially isotopically labeled peptides or proteins.

Elsewhere in this patent application, "peptide" can be read to include "protein" or "modified peptides or proteins".

In other embodiments, proteins or peptides can be captured for analysis by mass spectrometry by using a tagging moiety comprising three covalently-connected parts:

M-L-R wherein M is a magnetic particle; L is a linker that is covalently attached to M and contains zero or more atoms in a straight or branched chain and an optional selective cleavage site; and R is a specific reactive group including one of the reactive groups specified above ($R_S$, $R_C$, $R_L$, or $R_P$) that reacts with peptides or proteins. In this embodiment, tagged peptides or proteins may be isolated from untagged peptides or proteins by selective application of magnetic force on the M moiety, rather than by selective reagent capture of a B moiety.

Peptides can derive from enzymatically-digested proteins or be processed in other biological or synthetic means. Proteins can be isolated from, e.g., a patient cell sample, a patient serum sample, or a patient tissue sample. The proteins can be derived from, e.g., cultured cells, cultured cells treated with a compound of interest (e.g., a therapeutic compound or a potential therapeutic compound), or plant cells, microbial cells, a virus, or genetically modified cells.

In various embodiments $R_C$ comprises a thiol specific reactive group (e.g. a maleimide group or a pyridyl-dithio group), $R_L$ comprises an amine specific reactive group (e.g. a succinimide group), and $R_{S/T}$ comprises a Thr/Ser specific reactive group (e.g. a hydrazide group). $R_P$ may be comprised of $R_{S/T}$, $R_C$, $R_L$ or an enzymatic substrate or other element of molecular recognition such as antibodies, or ATP, GTP, NAD, NADP, NADH, NADPH, ubiquitin, or structural analogs thereof.

L is a single or multipart linker that may be composed of biological or nonbiological oligomeric structure. For example, L can comprise a polypeptide chain of any sequence, a chain of identical amino acids (e.g., polyglycine or poly-alanine), a chain of alternating amino acids or a chain of various amino acids. L can include, for example: O, S, NH, CO, COO, COS, S—S, $CH_2$, an alkyl group, an alkenyl group, and alkynyl group an alkoxy group, or an aryl group. L may contain chemical or enzymatic cleavage sites to enable the release of modified peptide or protein from M. L may or may not be differentially labeled with stable or radioactive isotope atoms.

In certain embodiments L is cleavable and contains a disulfide group or a vicinal diol group, or an ortho-nitrobenzyl ether, and in certain embodiments L is isotopically labeled, and/or R is isotopically labeled.

A variety of cleavage sites, either chemical or enzymatic or both, can be included in L. For example chemical cleavage there can be a disulfide bond that is cleaved using a suitable reducing agent. A glycol or diol bond can be cleaved by oxidation. A diazo bond can be cleaved using dithionite. An ester can be cleaved using hydroxylamine, acid, or base. A sulfone can be cleaved using a suitable base. Where L includes a polypeptide, it can be cleaved using a protease. A glycerol ester can be cleaved using a lipase. A phospho-ester can be cleaved using phosphatase. Polynucleotides or oligonucleotides can be cleaved using a nuclease.

In various embodiments the releasing step comprises exposing the captured tagged polypeptides to reducing agents or other cleavage reagents, and the released modified peptides are separated by chromatography prior to analysis by mass spectrometry. In other embodiments the captured tagged peptides are first treated to release B from the capture reagent (or to release M from capture from a magnetic field) and then treated to release the modified peptide or protein portion from B and all or part of L (or from M and all or part of L).

The M, L, and R moieties can be connected synthetically in a number of ways. For example, commercially available magnetic particles with the structure M-L-$NH_2$ can be purchased. Analogously, commercially available capture groups with the structure B-L-$NH_2$ may be purchased. The amino group can be reacted with various bifunctional cross-linking agents so as to create various R groups attached to either M or B through L.

Tagging moieties in which R is covalently attached to a magnetic particle have several advantages. First, they can be used to capture peptides in a single step. This allows for greater efficiency and ease of sample handling compared to methods in which peptides are first tagged with a reagent that includes an affinity label followed by capture of the affinity label on a solid support, e.g., a bead or solid particle, that is coated with a capture reagent that binds to the affinity label. Tagging moieties in which R is covalently attached to a magnetic particle or the solid phase material avoids the need for carrying out two binding steps in order to link the captured peptide to the solid support. In addition, by using a solid support, e.g., a M-L-R structure, sample clean up and removal of non-derivitized peptides can be accomplished in a single step. The capture can thus be faster and more efficient. Moreover, since the tagged peptides are isolated using a magnetic force to attract the magnetic particle, the capture step is not one that is subject to interference by components present in the reaction mixture, e.g., peptides, impurities, and is unaffected by such factors as buffer conditions and temperate. Moreover, magnetic particles provide many advantages in ease of sample handling. A suitable tagging moiety of the form M-L-R can be prepared as follows. A magnetic particle (the M portion) having a covalently-bound primary amino group Dynal A/S (Oslo, Norway) can be activated by reaction with N-succinimidyl-3-(2-pyridyldithio)propionate (SPDP), a heterobifunctional crosslinker available from Pierce Chemical Company. This reagent provides a pyridine thiol group that can be displaced by the thiol of a thiol-containing peptide. The peptide may also be a synthetic peptide that also includes a primary amino group to which a different R group may be attached. Thus, the thiol-containing peptide makes up a portion of the L group. The thiol-containing peptide can be labeled, e.g., with $^{13}$C or deuterium. In such cases, the M-L-R moiety is designated as M-L*-R. The isotope labeling allows for the relative quantification of peptides or proteins in different samples that are mixed together and analyzed by mass spectrometry simultaneously. The thiol-containing peptide preferably contains a cleavage site to allow for release of the captured peptide. Examples of cleavage sites include those with disulfide groups, that allow for chemical cleavage, or groups that allow for enzymatic cleavage, e.g., by trypsin. Peptides are desirable L groups, in part, because they are rather easy and relatively simple to synthesize. Because they can be designed to be substantially hydrophilic, substantially hydrophobic, or neither, they can be adapted to a variety of solution conditions. Moreover, peptides have structural and conformational flexibility. A peptide can be readily designed to include chemical cleavage site, an enzymatic cleavage site or both types of cleavage sites.

As noted above, the primary amino group of the thiol-containing peptide can react with various moieties to create varying R portions to the structure M-L-R (or B-L-R). For example, the primary amino group can react with a moiety including a hydrazide group. In this case, the R moiety will be selective for peptides with the threonine or serine at the amino terminus. Alternatively, the primary amino group can react with a moiety containing a malemide group. In this case, the R moiety will react selectively with cysteine-containing peptides. Other electrophilic R groups suitable for reacting with cysteine-containing peptides include: epoxides, α-haloacyl, nitriles, sulfonated alkyl thiols, and sulfonated aryl thiols. The R moiety can also include a succinimide group for reaction with an amino group (e.g., lysine).

The M-L-R or B-L-R moiety can be used to react with: (1) peptides, including those arising from enzymatic digestion of proteins; (2) proteins in a native form; (3) proteins in a denatured form and (4) proteins in their native, membrane-embedded form.

In the case of proteins in a native form (and certain peptides large enough to assume a secondary structure), only those specific amino acids that are presented (i.e., sterically available) on the outer part of the molecule will react with the M-L-R or B-L-R moiety. Therefore, the attachment allows for the specific targeting of "presented" parts of the protein. In the case of denatured protein, all parts of the protein are potentially accessible. The protein may subsequently be digested into peptide components. An M-L-R moiety can be used to capture a protein in its native or denatured form. The protein can then be digested chemically or enzymatically. The M-L-R moieties (with attached peptides) can be washed to remove unbound peptides (and other unwanted material). Subsequently, the modified peptides are released. In some cases it may be desirable to conduct more than one washing step. For example, tagged peptides or tagged polypeptides can be washed before or after capture or both.

In the case of tagging polypeptides or proteins prior to enzymatic or chemical digestion several approaches are possible. For example, a portion of a polypeptide present in a sample can be captured an analyzed by: (a) providing a tagging moiety having the formula: R-L-M, wherein R is a reactive group that reacts with polypeptides comprising a selected amino acid, L is a linker group, and M is a magnetic particle that can be attracted by a magnetic force; (b) reacting the sample with the tagging moiety to provide a tagged polypeptide; (c) isolating the tagged polypeptide by applying a magnetic force that attracts M to provide an isolated tagged polypeptide; (d) enzymatically or chemically digesting the isolated tagged polypeptide to provide an isolated tagged polypeptide fragment; (e) releasing at least the polypeptide fragment portion of the isolated tagged polypeptide fragment from the M group to provide a released modified polypeptide fragment; and (f) analyzing the released modified polypeptide fragment by mass spectrometry. In this method the digestion step takes place after the tagged polypeptides have been isolated. The order of the steps can be changed so that the digestion takes place prior to isolation of the tagged polypeptides. In this approach the method includes: (a) providing a tagging moiety having the formula: R-L-M, wherein R is a reactive group that reacts with polypeptides comprising a selected amino acid, L is a linker group, and M is a magnetic particle that can be attracted by a magnetic force; (b) reacting the sample with the tagging moiety to provide a tagged polypeptide; (c) digesting the tagged polypeptide provide an tagged polypeptide fragment; (d) isolating the tagged polypeptide fragment by applying a magnetic force that attracts M to provide an isolated tagged polypeptide fragment; (e) releasing at least the polypeptide fragment portion of the isolated tagged polypeptide fragment from the M group to provide a released modified polypeptide fragment; and (f) analyzing the released modified polypeptide fragment by mass spectrometry.

Intact proteins or polypeptides can also be tagged using an R-L-B tagging moiety. Thus, the invention includes a method comprising (a) providing a tagging moiety having the formula: R-L-B, wherein R is a reactive group that reacts with polypeptides comprising a selected amino acid, L is a linker group, and B is a group that can selectively bind to a capture reagent; (b) reacting the sample with the tagging moiety to provide a tagged polypeptide; (c) contacting the tagged polypeptide fragment with the capture reagent to provide a captured tagged polypeptide; (d) digesting the captured tagged polypeptide to provide a captured tagged polypeptide fragment; (e) releasing at least the polypeptide portion of the capture tagged polypeptide fragment from the B group to provide released modified polypeptide fragment; and (f) analyzing the released modified polypeptide fragment by mass spectrometry. The invention also includes a method comprising: (a) providing a tagging moiety having the formula: R-L-B, wherein R is a reactive group that reacts with polypeptides comprising a selected amino acid, L is a linker group, and B is a group that can selectively binds to a capture reagent; (b) reacting the sample with the tagging moiety to provide a tagged polypeptide; (c) digesting the tagged polypeptide provide an tagged polypeptide fragment; (d) contacting the tagged polypeptide fragment with the capture reagent to provide a captured tagged polypeptide fragment; (e) releasing at least the polypeptide fragment portion of the captured tagged polypeptide fragment from the B group to provide a released modified polypeptide fragment; and (f) analyzing the released modified polypeptide fragment by mass spectrometry.

When polypeptides or proteins are tagged using one of the tagging moieties of the invention, it should be understood that the polypeptide or protein is not necessarily an intact, naturally occurring polypeptide or protein (although it may be). In some a naturally occurring or polypeptide can be subjected to preliminary treatment that reduces it size before it is tagged.

In another embodiment specifically to address membrane embedded and/or insoluble proteins, a tagging moiety comprising the structural group M, L, Sol, and R can be used for simplifying protein and peptide mixtures for analysis by mass spectrometry. In this tagging moiety M is a magnetic particle, L is a linker group, Sol is a membrane-impermeable solublizer group and R is a chemically reactive group that can selectively bind with specific amino acids or modified amino acids, such as those described above. The solublizer group can be a polymeric species, such as polyethylene glycol (PEG) or methoxylated polyethylene glycol (MPEG), that enhances solubility of protein that is linked to the R group. This approach is particularly useful when the protein itself is not be sufficiently soluble in aqueous solution once removed from its membrane. Various arrangements of these components can be used including:

M-L-Sol-R,

M-Sol-L-R,

M-L-Sol-L-R,

M-L-R-Sol,

M-L-R-L-Sol, and

M-L-R

☐

Sol

One or more chemical cleavage sites (e.g., as described above) may be provided between the M, Sol or R groups, but in the most preferred embodiments the L group includes a cleavage site near the magnetic particle to yield, after cleavage, the peptide for protein linked to R, L and Sol. The cleavage site may be comprised of a disulfide or an enzyme-cleavable oligo-peptide. Thus, after cleavage the Sol group enhances the aqueous solubility of bound protein. The enhanced solubility may be beneficial for the processes to which the protein must be exposed prior to analysis by mass spectrometry utilizing fluid ionization techniques such as electrospray. A second cleavage site can be used to release the Sol group leaving the peptide or protein linked to all or part of R and all or part or none of L.

Optionally, one or more of L, R and Sol may be isotopically labeled.

As discussed above, a B group can be used in place of an M group. Thus, biotin or some other affinity base can be used in place of a magnetic particle. Under these circumstances, the tagged peptide can be captured using, for example, a streptavidin-coated magnetic particle. In this case, the solubilizer consisting of R, L, Sol and B also can play the function of preventing transfer of the amino acid-specific reagent (R) across lipid membranes. Thus, the agent is effective to select specific intramembrane proteins that present an aspect to the exterior of the lipid membrane and, in addition, solubilizes these proteins during the proteolytic and other sample preparation steps upstream of LCMS analysis.

There are also applications for a general solubilizing agent consisting of R, L, and Sol for generally solubilizing membrane-bound protins. A solid-phase capture is not always required. For example, various liquid chromatographic means can be used to isolate the membrane-derived components.

The invention also features reagent kits comprising tagging moieties having the formulae:

R-L-B

R-L-M

R, L, Sol and M

R, L, Sol, and B, and

R, L, and Sol wherein R includes one of the above four reactive groups ($R_{S/T}$, $R_C$, $R_L$, or $R_P$) as described in detail above, L is a linker group as described above, B is a group that can selectively bind a capture reagent as described above; and optionally a proteolytic enzyme. In various embodiments L or R is isotopically labeled (denoted L* or R*), $R_S$ contains a structure of the formula —CO—NH—NH$_2$, and the entire tagging moiety is biotin hydrazide.

In other embodiments the reagent kit further comprises: a capture reagent, a capture reagent comprising avidin or streptavidin bound to a solid support such as a latex particle or magnetic particle; D-biotin; an oxidizing agent (e.g., sodium metaperiodate) and an agent capable of quenching the oxidizing agent, and buffers formulated specifically to optimize the reactions and separations involved In other embodiments, the analysis by mass spectrometry comprises determining the molecular weight of at least one released modified peptide and/or the amino acid sequence of at least a portion of at least one released modified peptide and the peptides are treated chemically prior to reacting with the tagging moiety.

The methods of the invention are useful, in part, because the analysis of complex peptide mixtures can be very difficult and time consuming. Peptide mixtures generated by enzymatic digestion or other means from whole cell extracts, organelles, protein complexes, or tissue samples can contain a extraordinarily large number of peptides. For example, a tryptic digest of a whole mammalian cell lysate can contain 1,000,000 or more peptides. Analyzing the amount, much less the identity of each peptide in such a mixture is a daunting task. Attempting to identify the proteins from which the peptides were generated further increases the complexity of the analysis. However, as can be appreciated by those skilled in the art, a given protein present in a mixture can be identified and quantified based on one or a few of the peptides generated by digestion of the protein. It is a commonly accepted practice in biology to identify the presence of a protein by the binding of an antibody specific to that protein, even though the antibody recognizes and binds to only a small fraction of the total structure of the protein. In other words, a protein can be identified by detecting fewer than all of the peptides arising from digestion of the protein. Thus, methods that reduce the complexity of peptide mixtures in a controlled and predictable manner by isolating a subset of peptides present in the mixture can greatly facilitate the identification and/or quantification of the proteins from which the peptide mixture was generated.

Analysis is facilitated because the time and memory required for database searching to identify the peptides present in the mixture (and the proteins from which they were derived) is greatly reduced. The increases in the speed, simplicity and confidence of analysis that are achieved by the methods of the invention can be realized with, at most, only a minor loss of information. This loss of information can occur, for example, because some small fraction of proteins will, under some conditions, fail to generate peptides that can be tagged with a given R group. Thus, under some circumstances, a small number of proteins will not be detected. However, the difficulty can be largely overcome by performing additional analysis. For example, a tagging moiety with a different R group can be used in additional analysis. In the case of a tagging moiety using a $R_{S/T}$ the proteins in the original mixed protein sample can be digested in an alternative manner that generates amino terminal ser peptides and/or amino terminal thr peptides from the proteins that do not generate such peptides under the first set of digestion conditions. This highlights one of the strong points of the described method, namely that it relies on sequence information that is present in the protein, which means that cutting the protein with an enzyme of different specificity will lead to a set of peptides that can be nearly orthogonal to the original set. The results from the secondary analysis can be combined with the results of the primary analysis to create a complete analysis of the proteins present in the original sample.

Other features and advantages of the invention will be apparent from the following detailed description and claims.

DETAILED DESCRIPTION OF THE INVENTION

Figure 1:
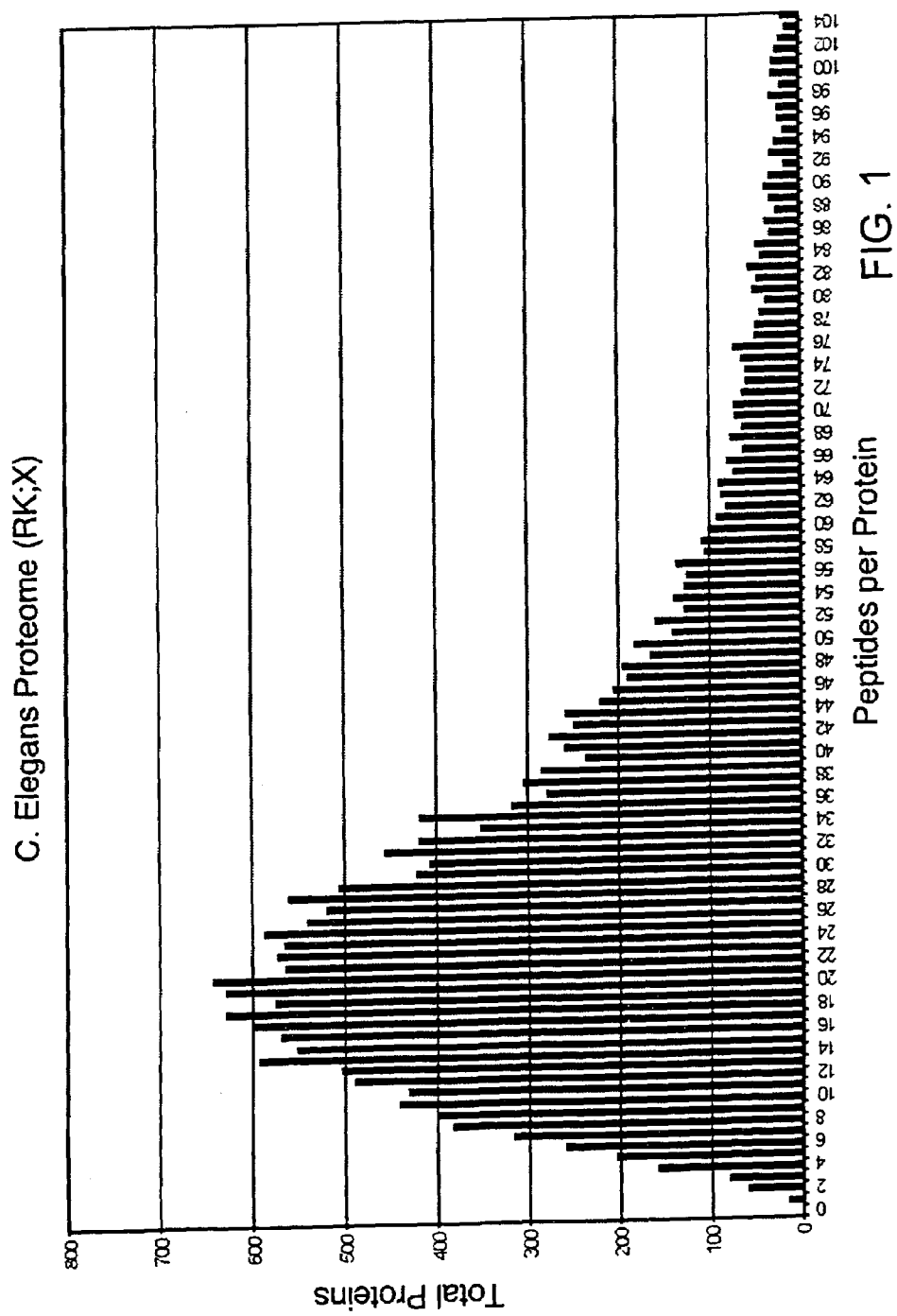
FIG. 1 depicts the distribution of peptides/protein generated by bioinformatic modeling of a trypsin digestion of the entire proteome of *C. elegans*.

Using the methods of the invention complex peptide mixtures can be simplified by isolating peptides which include particular amino acids (e.g., peptides having an amino terminal serine ("amino terminal-ser peptides") or an amino terminal threonine ("amino terminal-thr peptides")). The peptides are isolated by reacting the peptides with a tagging moiety which reacts with the desired peptides and tags them for capture by a capture reagent. The tagging moiety includes a reactive group (R), a linker group (L), and a group (B) that can selectively bind to a capture reagent or, in place of B, a magnetic group (M) that responds to a magnetic force. The tagged peptides are captured and isolated either by contacting them with a capture reagent (e.g., a capture reagent bound to a solid support) where the tagging moiety includes a B group or by attracting the tagged peptide with an applied magnetic force where the tagging moiety includes an M group. Depending on the type of R group used, cysteine-containing peptides, lysine-containing peptides or peptides having either an amino terminal-serine or an amino terminal-threonine can be isolated from other materials present in the mixture (e.g., other peptides). After isolation, the captured peptides are released from the capture reagent and analyzed by mass spectroscopy. The peptides can be released by selectively cleaving the linker group within the tagging moiety or by disrupting the interaction between the capture reagent and the group that selectively binds to the capture reagent. In many cases the released peptides are modified peptides in that they may include components derived from the tagging moiety, e.g., all or part of the linker group (L) and/or all or part of the reactive group (R). In some cases it may be possible to release the peptide in an essentially unmodified form.

The capture reagent can be avidin or streptavidin or modified avidin or strepavidin and the tagging moiety can include biotin or a modified biotin. Alternatively, the capture reagent can be biotin or a modified biotin and the tagging moiety can include avidin or streptavidin or modified avidin or streptavidin. In order to facilitate isolation of the tagged peptides from other components, the capture reagent can be bound, preferably covalently, to a solid support such as glass particles, the well of a microtiter plate, magnetic particle or the like. Thus, the tagged peptides can be captured using avidin or streptavidin coated magnetic particles.

The peptides, e.g., the amino terminal-ser and amino terminal-thr peptides, can be generated by cleavage of a protein or a mixture of proteins. The cleavage can be enzymatic. For example, peptides can be generated by digestion a protein or mixture of proteins with trypsin using standard techniques.

Amino terminal-ser and amino terminal-thr peptides for analysis by mass spectrometry can be prepared as follows. A sample containing mixture of proteins is subjected to denaturing conditions. The denatured proteins are digested with trypsin. The beta-amino alcohol moiety present on amino terminal-ser peptides and amino terminal-thr peptides is selectively oxidized by adding, to the peptide mixture dissolved in pH 7 phosphate buffer, sodium metaperiodate to make the solution 40 mM in periodate. After incubation at room temperature in the dark for 5 minutes, the excess oxidant is quenched by the addition of ethylene glycol. The modified peptides are then biotinylated by adding biotin hydrazide directly to the reaction mixture and incubating for 30 minutes. The selectively biotinylated peptides are then captured on monomeric-streptavidin coated particles. After washing away non-modified peptides and washing with HPLC starting buffer, the peptides are eluted from the particles by displacement with free D-biotin. Alternatively, a specialized biotin-hydrazide that contains a cleavable linker can be used for the biotinylation step and a selective cleavage reagent can be added to release the bound peptides from the particles. Examples of cleavable groups that can be incorporated into the linker include a disulfide group (cleaved with TCEP), or a vicinal diol group (cleaved with sodium periodate). Once the isolated peptides have been released from the particles, they can be analyzed directly by injecting the sample into the liquid chromatography-mass spectrometry equipment (LC/MS).

Previously described methods for achieving simplification of peptide mixtures have utilized the reactive sulfhydryl group of cysteine (cys) to isolate peptides containing a cys. By isolating peptides having an amino terminal-ser or an amino terminal-thr, the methods of the present invention can result in even greater simplification with little or no increase in the number of proteins missed. In general, increased simplification and knowledge of partial sequence information permits one to conduct more constrained database searches and results in smaller databases with faster searches, requiring less intensive use of processing capacity and memory. Moreover, in the methods of the invention, a portion of each peptide analyzed is known (e.g., it is known that there is an amino terminal ser or thr or it is known that a cys is present or it is known that a lys is present). This constrains the database searching and facilitates the interpretation of MS/MS fragmentation patterns. Moreover, analysis of peptides that are modified at the amino terminus may be easier than analysis of internally modified peptides. The methods of the invention reduce the need for peak parking and hence result in increased sample throughput since occurrence of co-eluting peaks should decrease.

Figure 2:
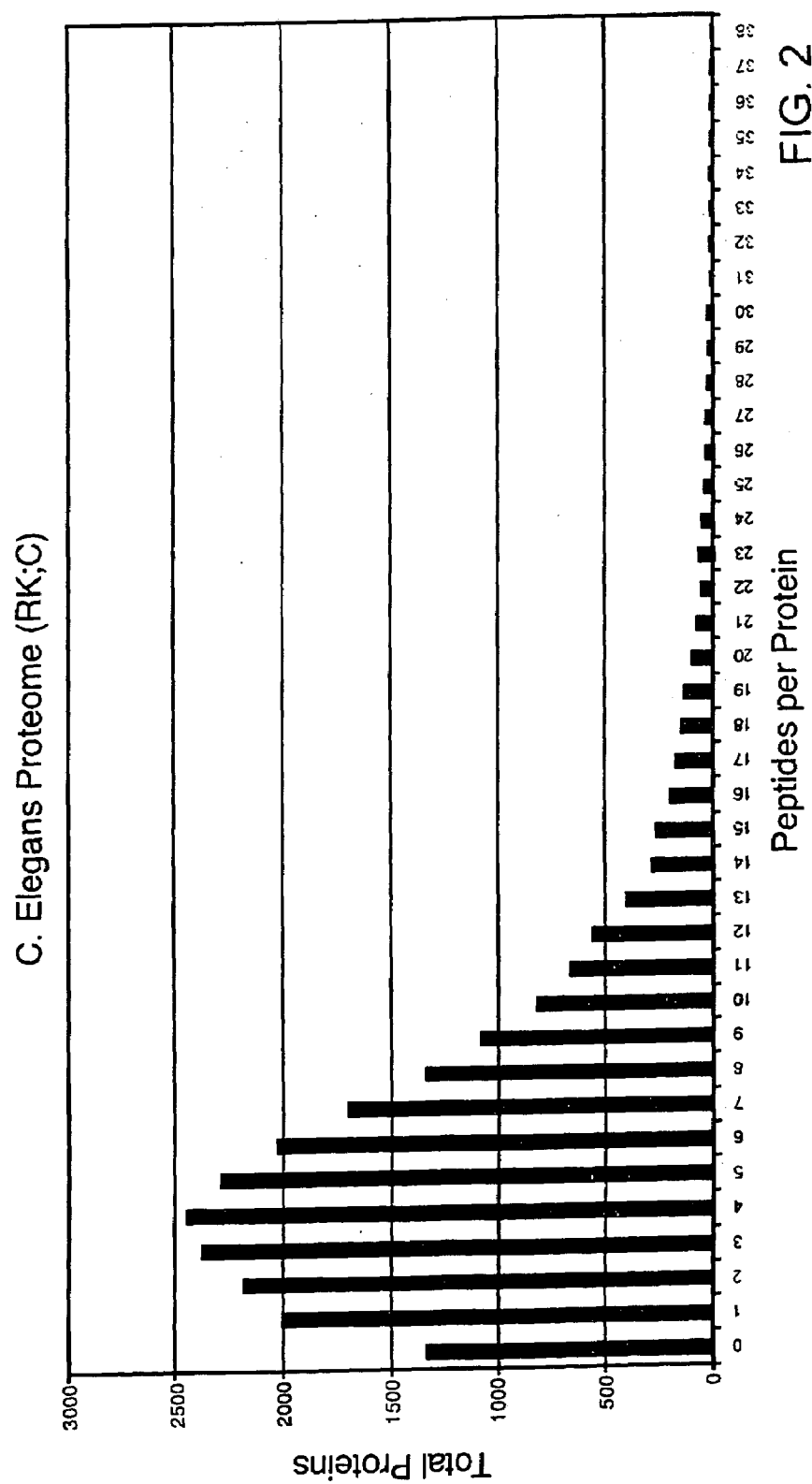
FIG. 2 depicts the distribution of cys-containing peptides/protein generated by bioinformatic modeling of a trypsin digestion of the entire proteome of *C. elegans* followed by selection of cys-containing peptides.
Figure 3:
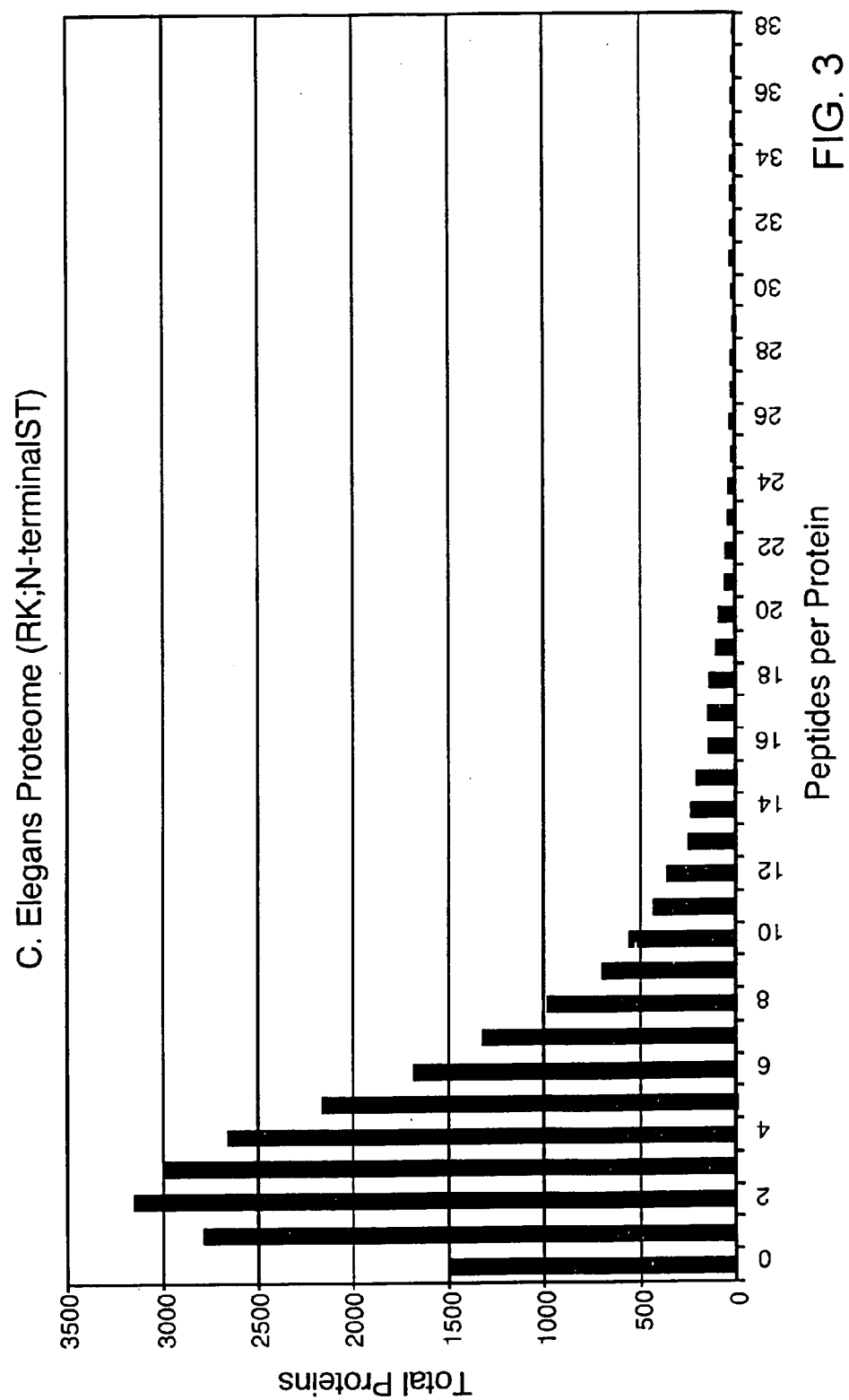
FIG. 3 depicts the distribution of amino terminal-ser and amino terminal-thr peptides/protein generated by bioinformatic modeling of a trypsin digestion of the entire proteome of *C. elegans* followed by selection of amino terminal-ser and amino terminal-thr peptides.

The simplification achieved by the present method can be illustrated by examining the proteome resulting from a complex genome. FIGS. 1–3 depict the results of bioinformatic analysis of a trypsin digestion of the entire C. Elegans proteome. FIG. 1 depicts the distribution of peptides/protein generated by trypsin digestion of the entire proteome. FIG. 2 depicts the distribution of cys-containing peptides/protein generated by trypsin digestion of the entire proteome. FIG. 3 depicts the distribution of amino terminal-ser and amino terminal-thr peptides/protein generated by trypsin digestion of the entire proteome. The results of these calculations suggest that the greater simplification may be achieved by selecting amino terminal-ser and amino terminal-thr peptides than by selecting cys-containing peptides. These calculations suggest that about 5% of the proteome is not detectable with each approach (the fraction of proteins having 0 peptides/protein). These calculations have discarded resulting peptides containing 3 or less amino acids as a result of enzymatic cleavage.

Figure 4:
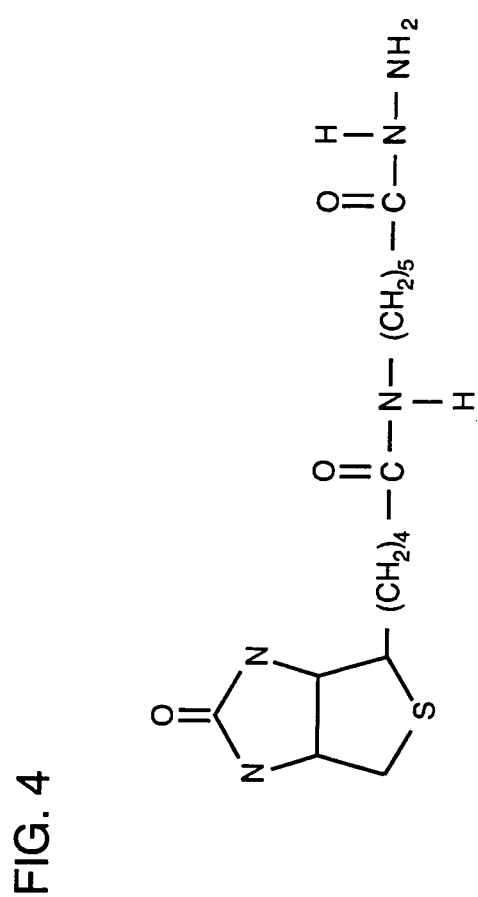
FIG. 4 depicts the structure of biotin hydrazide.

FIG. 4 depicts the structure of biotin hydrazide. This compound is an example of a B-L-$R_{S/T}$ tagging moiety. It includes an B group comprising biotin 2 an L group 4, and a $R_{S/T}$ group comprising a hydrazide group 6.

Figure 5A:
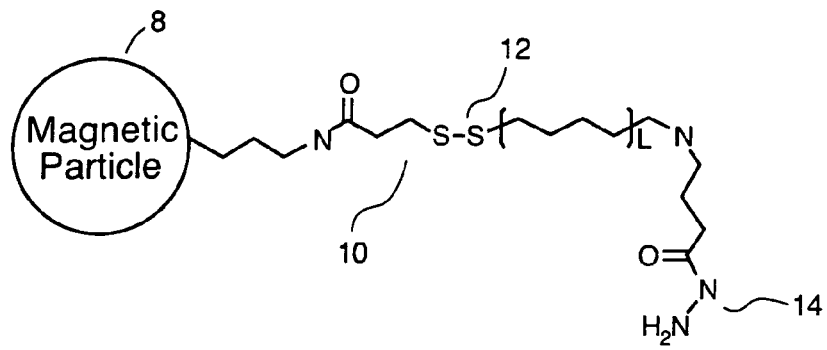
FIGS. 5A–5C depict various M-L-R tagging moieties.
Figure 5B:
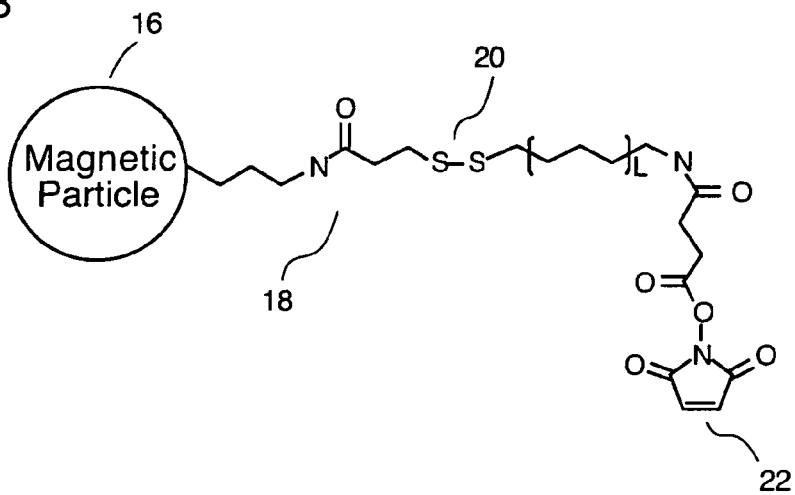
Figure 5C:
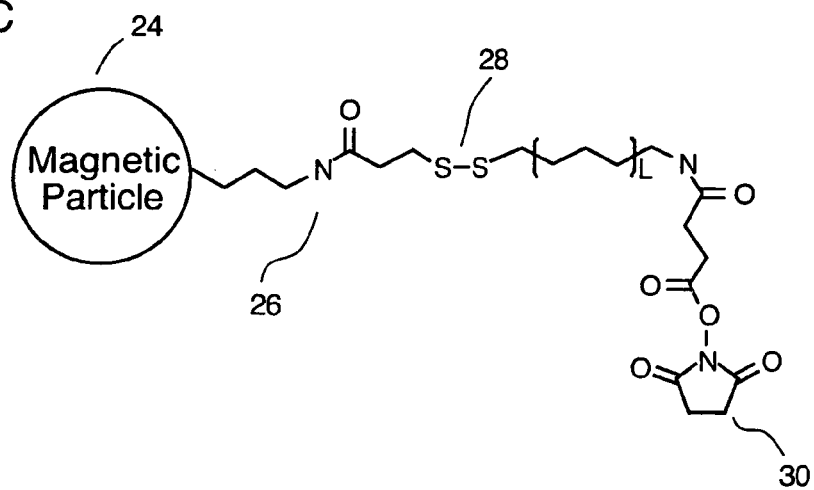

FIGS. 5A–5C depict exemplary combination of M, L, and R (i.e., M-L-R tagging moiety). FIG. 5A depicts a tagging moiety suitable for capture of peptides having an amino terminal Ser or Thr. The tagging moiety includes a magnetic particle 8, an L group 10 that includes a disulfide bond cleavage site 12, and a reactive group that includes a hydrazide group 14. FIG. 5B depicts a tagging moiety suitable for capture of peptides having a Cys. The tagging moiety includes a magnetic particle 16, an L group 18 that includes a disulfide bond cleavage site 20, and a reactive moiety that includes a malemide group 22. FIG. 5C depicts a tagging moiety suitable for capture of peptides having a Lys. The tagging moiety includes a magnetic particle 24, an L group 26 that includes a disulfide bond cleavage site 28, and a reactive moiety that includes a succinimide group 30.

The tagging moiety can be isotopically labeled, e.g., by substituting one or more atoms in the linker group or the reactive moiety with a stable isotope of the atom, e.g., one or more hydrogens can be replaced with deuterium or one or more $^{12}C$ can be replaced with $^{13}C$ or $^{14}N$ can be labeled with $^{15}N$, or combinations thereof. When an isotopically labeled tagging moiety is used, the released modified peptides will be isotopically labeled. When two peptide samples are reacted with differentially isotopically labeled, but chemically identical, tagging moieties, quantification of the relative amount of the peptides in the two samples is facilitated. This is because a mixture of the two peptide samples one modified with the "light" form of the tag and one modified with the "heavy" form of the tag will contain a light form and a heavy form of two chemically identical entities. Thus, This approach has been used to quantify cys-containing peptides (Gygi et al. (1999) Nature Biotech. 17:994; and PCT Publication WO 00/11208) and a similar approach can be used to quantify amino terminal-ser and amino terminal-thr peptides and lys-containing peptides.

Two different peptide samples, e.g., one sample derived from cells exposed to a selected compound and one sample derived from cells not exposed to the selected compound can be differentially isotopically labeled using the tagging moieties of the present invention. The isolated modified differentially isotopically labeled peptides arising from the two samples can be mixed together and analyzed by mass spectrometry.

Figure 6:
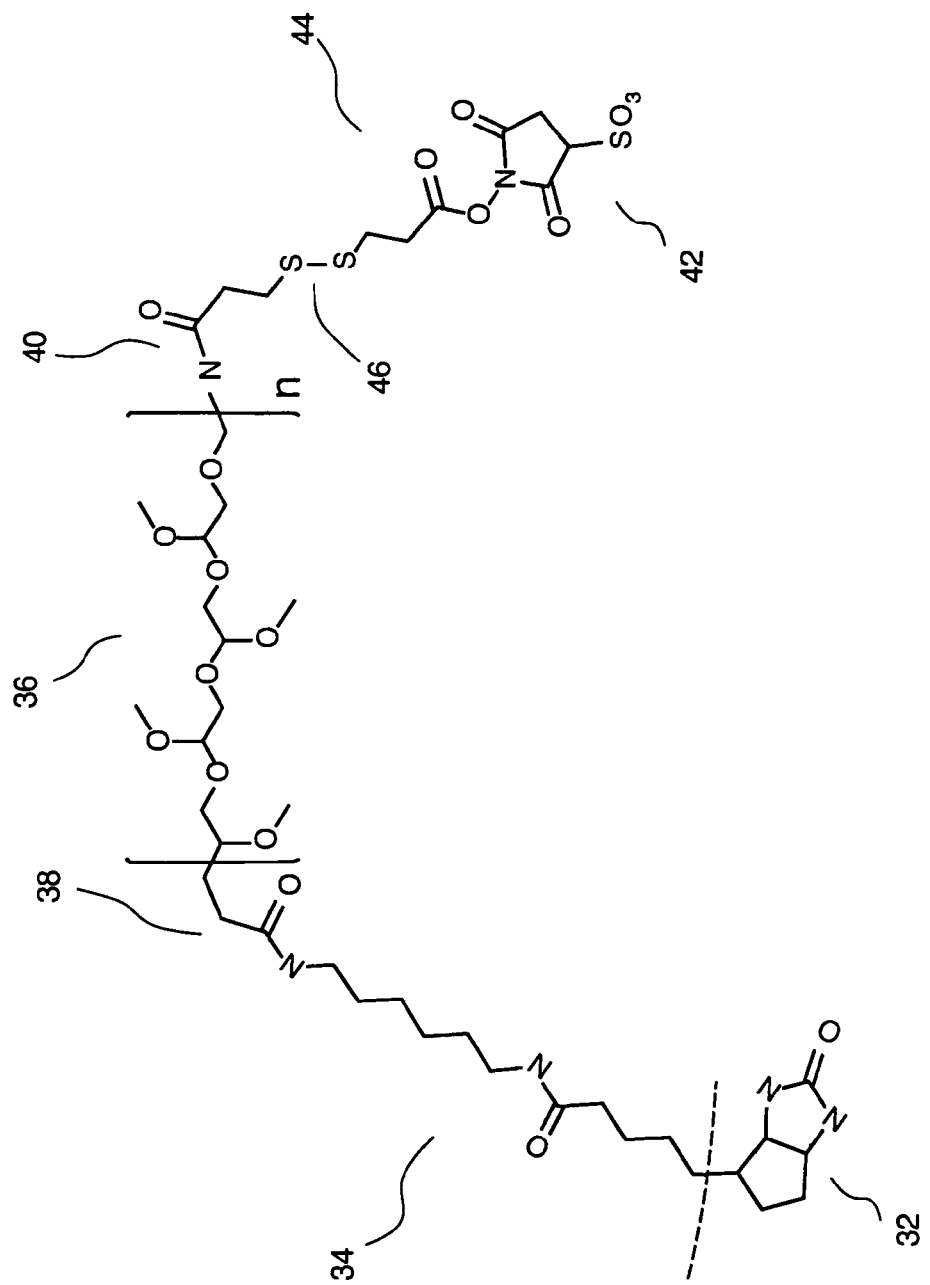
FIG. 6 depicts a B-L-Sol-L-R tagging moiety.

FIG. 6 depicts an example of a B-$L_A$-Sol-$L_B$-R tagging moiety. The R group of this tagging moiety is biotin 32 the $L_B$ group 34 is a chain that is at least 13 Å long. A Sol group 36 comprising methoxy polyethylene glycol (MPEG) is connected at one end to the $L_B$ group by an amide bond 38 and at the other end to the remainder of the tagging moiety by an amide bond 40. The MPEG can be as much as or more than 5,000 Daltons in mass and can include one or more nucleophilic or electrophilic groups for reaction with the L group and the R group. The Sol group 36 is connected to the R group 42 by a second linker region $L_A$ 44 that includes a readily cleavable disulfide bond 46. The R group 42 is a succinimide group that can selectively react with amine groups (e.g., lysine containing peptides).

EXAMPLE

Bovine serum albumin (BSA; Sigma Chemical, Inc.) and horse myoglobin (Sigma Chemical, Inc.) were separately digested with trypsin (Promega, Inc.) according to standard procedures. The peptide mixtures obtained from the digestions were treated with $NaIO_4$. Next excess oxidant was quenched by the addition of ethylene glycol. The modified peptides were then selectively biotinylated by incubating the peptide mixtures with biotin hydrazide (Pierce Chemical, Co.; FIG. 4) for 30 minutes. The biotinylated peptides were captured using MPG streptavidin-coated magnetic particles (CPG, Inc.). Sample processing was performed with a KingFisher automated magnetic particle processor (Lab Systems, Inc).

The samples were analyzed using a Surveyor HPLC (ThermoFinnigan, Inc), configured for nanoflow operation, coupled to a nanospray source-equipped LCQ Deca mass spectrometer (ThermoFinnigan, Inc.). Reverse phase-HPLC was performed using a PicoFrit packed tip (New Objective) (75 um i.d. by 10 cm length) and standard reversed-phase gradients at a flow rate of 100 nL/min.

Based on the sequence of BSA, trypsin digestion should yield six thr/ser amino terminal peptides. Based on the sequence of horse myoglobin, trypsin digestion should yield one thr/ser amino terminal peptide. The six expected peptides for BSA and the one expected peptide for myoglobin were the only peptides observed in the captured fraction.

The contents of all references, patents and published patent applications cited throughout this application are hereby incorporated by reference.

Other Embodiments

Two or more tagging moieties with differing R groups can be used in combination. A tagging moiety that is capable of selectively reacting with cys-containing peptides can be used to isolate cys-containing peptides from one fraction of a sample of interest. A tagging moiety capable of selectively reacting with amino terminal-ser and amino terminal-thr peptides can be used to isolated amino-terminal-ser and amino terminal-thr peptides from a second fraction of the sample of interest. The modified peptides isolated using both types of tagging moieties can be combined and analyzed by mass spectrometry or they can be independently analyzed and the results combined. If the tagging moieties can be captured using the same capture reagent, the tagged peptides (a mixture of cys-containing, amino terminal-ser, and amino terminal-thr peptides) can be captured with the capture reagent in a single reaction. The mixture of released, modified peptides can then be analyzed by mass spectrometry. Differentially isotopically labeled tagging moieties can be used to differentially label the peptides in two or more different samples. The released peptides can be analyzed by methods other than mass spectrometry. Thus, the various tagging moieties and methods of the invention can be used to isolated and purify peptides or simplify complex mixtures for any purpose.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method for analyzing a protein sample using a subset of peptides produced from the protein sample; the method comprising:
   (a) first digesting proteins in the protein sample to produce a set of digested peptides, the set including one or more peptides having an amino terminal serine or an amino terminal threonine;
   (b) providing a tagging moiety having the formula:

R-L-B wherein R is a reactive group that reacts with the amino terminal serine or an amino terminal threonine of the digested peptides, L is a linker group containing zero or more atoms, and B is a group that can selectively bind to a capture reagent;
   (c) reacting the set of peptides with the tagging moiety to provide a subset of tagged peptides;
   (d) contacting the subset of tagged peptides with the capture reagent to provide captured tagged peptides;
   (e) releasing at least peptide portions of the captured tagged peptides from the capture reagent to provide released modified peptides; and
   (f) analyzing the protein sample by analyzing the released modified peptides using mass spectometry.

2. The method of claim 1 wherein R comprises —CO—NH—NH2 (hydrazide).

3. The method of claim 1 wherein B comprises biotin.

4. The method of claim 1 wherein B comprises d-iminobiotin.

5. The method of claim 3 wherein the capture reagent comprises avidin or streptavidin.

6. The method of claim 3 where in the releasing step comprises exposing the captured tagged polypeptides to biotin.

7. The method of claim 3 wherein the capture reagent comprises an antibody selective for biotin.

8. The method of claim 1 wherein the tagging moiety is biotin hydrazide.

9. The method of claim 1 wherein the sample is exposed to an oxidizing agent prior to exposing the sample to the tagging moiety.

10. The method of claim 1 wherein L comprises a disulfide group.

11. The method of claim 1 wherein L comprises a vicinal diol group.

12. The method of claim 1 wherein L is isotopically labeled.

13. The method of claim 1 wherein the released modified peptides are separated by chromatography prior to analysis by mass spectrometry.

14. The method of claim 1 wherein R is isotopically labeled.

15. The method of claim 1 wherein the analysis by mass spectrometry comprises identifying at least one peptide.

16. The method of claim 1 wherein the analysis by mass spectrometry comprises quantifying at least one peptide.

17. A method for analyzing a polypeptide sample, the method comprising:
   (a) providing a tagging moiety having the formula:

R-L-B wherein R is a reactive group that reacts with an amino terminal serine or an amino terminal threonine of a digested polypeptide, L is a linker group containing zero or more atoms, and B is a group that can selectively bind to a capture reagent;
   (b) reacting a previously digested polypeptide sample, produced by previously digesting proteins in a protein sample, with the tagging moiety to provide tagged polypeptides;
   (c) contacting the tagged polypeptides with the capture reagent to provide captured tagged polypeptides;
   (d) digesting the captured tagged polypeptides to provide captured tagged polypeptide fragments;
   (e) releasing at least polypeptide fragment portions of the captured tagged polypeptide fragments from the B group to provide released modified polypeptide fragments; and
   (f) analyzing the polypeptide sample by analyzing the released modified polypeptide fragments using mass spectrometry.

18. The method of claim 17 wherein L is isotopically labeled.

19. The method of claim 17 wherein R is isotopically labeled.

20. The method of claim 1, further comprising:
(a) providing a second tagging moiety having the formula:

R'-L-B wherein R' is a different reactive group than R that reacts with an amino acid of a digested peptide selected from cysteine, lysine, amino-terminal serine, or amino-terminal threonine;
(b) reacting the set of peptides with the second tagging moiety to provide a second subset of tagged peptides;
(c) contacting the second subset of tagged peptides with the capture reagent to provide a additional captured tagged peptides;
(d) releasing at least peptide portions of the additional captured tagged peptides from the capture reagent to provide additional released modified peptides; and
(e) characterizing the protein sample by analyzing the additional released modified peptides.

21. The method of claim 20, wherein:
the released modified peptides are analyzed together with the additional released modified peptides by mass spectrometry.

22. The method of claim 20, wherein:
R' is an isotopically labeled version of R.

23. The method of claim 8 wherein L is —NH(CH$_2$)$_5$—.

24. The method of claim 17, wherein further comprising:
(a) providing a second tagging moiety having the formula:

R'-L-B wherein R' is a different reactive group than R that reacts with an amino acid of a digested peptide selected from cysteine, lysine, amino-terminal serine, or amino-terminal threonine;
(b) reacting the polypeptide sample with the second tagging moiety to provide additional tagged polypeptides;
(c) contacting the additional tagged polypeptides with the capture reagent to provide additional captured tagged polypeptides;
(d) digesting the additional captured tagged polypeptides to provide additional captured tagged polypeptide fragments;
(e) releasing at least additional polypeptide fragment portions of the additional captured tagged polypeptides from the B group to provide additional released modified polypeptide fragments; and
(f) analyzing the polypeptide sample by analyzing the additional released modified polypeptide fragment fragments using mass spectrometry.

* * * * *